United States Patent
Ruiz et al.

(10) Patent No.: US 7,225,811 B2
(45) Date of Patent: Jun. 5, 2007

(54) HEADGEAR APPARATUS

(76) Inventors: Sherrie E. Ruiz, 84050 Yellowjacket Rd., Milton Freewater, OR (US) 97862-6704; Antonio R. Ruiz, 84050 Yellowjacket Rd., Milton Freewater, OR (US) 97862-6704

( * ) Notice: Subject to any disclaimer, the term of this patent is extended or adjusted under 35 U.S.C. 154(b) by 0 days.

(21) Appl. No.: 10/402,635

(22) Filed: Mar. 28, 2003

(65) Prior Publication Data

US 2004/0083534 A1 May 6, 2004

Related U.S. Application Data

(60) Provisional application No. 60/422,427, filed on Oct. 30, 2002.

(51) Int. Cl.
*A62B 18/08* (2006.01)

(52) U.S. Cl. .................. 128/207.11; 128/848; 2/171.2; 2/183

(58) Field of Classification Search .................. 2/171.2, 2/183, 9; 128/207.11, 848, 207.13, 207.17, 128/206.27; 602/902, 17; D24/191
See application file for complete search history.

(56) References Cited

U.S. PATENT DOCUMENTS

| | | | | |
|---|---|---|---|---|
| 649,896 | A * | 5/1900 | Baughman .................. 128/848 |
| 1,235,419 | A * | 7/1917 | Bloomfield ................ 128/848 |
| 1,339,865 | A | 5/1920 | Rothenberger |
| 1,519,915 | A | 12/1924 | Johnson |
| 1,587,558 | A | 6/1926 | Sheffield |
| 1,629,892 | A * | 5/1927 | Storms ........................ 128/848 |
| 2,044,521 | A * | 6/1936 | Weiland et al. ............. 132/274 |
| 2,711,730 | A * | 6/1955 | Rogers ........................ 128/848 |
| 3,776,244 | A * | 12/1973 | Morgan ...................... 132/273 |
| 4,207,881 | A * | 6/1980 | Richter ........................ 602/17 |
| 4,934,357 | A * | 6/1990 | Frantzich et al. ............. 602/61 |
| 5,277,700 | A * | 1/1994 | Smith .......................... 602/74 |
| 5,361,416 | A | 11/1994 | Petrie et al. |
| 5,687,743 | A | 11/1997 | Goodwin .................... 128/848 |
| 5,724,965 | A * | 3/1998 | Handke et al. ........ 128/207.13 |
| 5,787,894 | A | 8/1998 | Holt ............................ 128/848 |
| 5,893,365 | A | 4/1999 | Anderson ................... 128/848 |
| D410,089 | S | 5/1999 | Schiavoni .................. D24/191 |
| 6,016,807 | A | 1/2000 | Lodge ........................ 128/848 |
| 6,119,694 | A | 9/2000 | Correa et al. .......... 128/207.13 |
| 6,269,814 | B1 * | 8/2001 | Blaszczykiewicz et al. ...... 128/207.17 |
| 6,279,577 | B1 | 8/2001 | Savaiano .................... 128/848 |
| 6,470,886 | B1 * | 10/2002 | Jestrabek-Hart ....... 128/207.11 |

FOREIGN PATENT DOCUMENTS

WO    WO 9420051 A1 * 9/1994

* cited by examiner

*Primary Examiner*—Rodney M. Lindsey
(74) *Attorney, Agent, or Firm*—Mark Bauman

(57) ABSTRACT

To this end, the present invention comprises a headgear apparatus comprising a sleeve, a first strap portion and a second strap portion. The sleeve comprises a chin portion and a top portion. The top portion is integrally connected to the chin portion. The first strap portion is connected to a first part of the sleeve near the top portion. The second strap portion is connected to a second part of the sleeve near the chin portion. A nosepiece may be fastened to the headgear apparatus via the first strap portion and the second strap portion.

23 Claims, 3 Drawing Sheets

HEADGEAR APPARATUS

This application claims the benefit of U.S. Provisional Application No. 60/422,427, filed Oct. 30, 2002.

FIELD OF THE INVENTION

The present invention is generally directed towards the field of headgear apparati and, more specifically, to headgear apparati directed to curing a variety of sleep disorders, such as, for example, sleep apnea and other oxygen-deprivation disorders.

BACKGROUND OF THE INVENTION

Sleep apnea (SA) is a serious, potentially life-threatening condition that is far more common than generally understood. First described in 1965, SA is a breathing disorder generally characterized by brief interruptions of breathing during sleep. Generally speaking, there are two types of SA. Central sleep apnea, which is less common, occurs when the brain fails to send the appropriate signals to the breathing muscles to initiate respirations or, conversely, when the breathing muscles do not receive such signals. Obstructive sleep apnea is far more common and occurs when air is prevented from flowing into or out of a person's nose or mouth, although efforts to breathe continue. A third form of sleep apnea exists, mixed sleep apnea, and is exactly that—a mixture of the other two forms.

In a given night for a person having SA, the number of involuntary breathing pauses, or "apneic events," may range from as low as one or two to as high as twenty or sixty per hour. These breathing pauses are almost always accompanied by snoring, although not everyone who snores is sleep apnetic. SA can also be characterized by choking sensations. In any event, the frequent interruptions of deep, restorative sleep often leads to excessive daytime sleepiness and may be associated with an early morning headache. Moreover, SA may be associated with irregular heartbeat, high blood pressure, heart attack and stroke.

SA occurs in all age groups and within both sexes; however, it is more common in men (although that may be because SA is underdiagnosed in women) and possibly young persons of African descent. Within the United States, it has been estimated that as many as 18 million Americans have SA. Four percent of middle-aged men and two percent of middle-aged women have SA, along with excessive daytime sleepiness. People most likely to have or develop SA include those who snore loudly and also who are overweight, and those who have high blood pressure or have some physical abnormality in the nose, throat or other parts of the upper respiratory airways. Additionally, SA seems to run in some families, suggesting a possible genetic basis.

Certain mechanical and structural anomalies in the respiratory airways of a sleep apnetic person cause the interruptions in breathing during sleep. In some people, SA onset occurs when the throat muscles and tongue relax during sleep and partially block the opening of the respiratory airways. When the muscles of the soft palate at the base of the tongue and the uvula relax and sag, the respiratory airway becomes blocked, making breathing labored and noisy or even stopping altogether. SA also can occur in obese people when an excess amount of tissue in the respiratory airways causes them to be narrowed. With a narrowed respiratory airway, the person continues efforts to breathe, but air cannot easily flow into or out of the nose or mouth. Unknown to the person, this results in heavy snoring, periods of no breathing and frequent arousals (causing abrupt changes from deep sleep to light sleep). Ingestion of alcohol and sleeping pills increases the frequency and duration of breathing pauses in people with SA.

During the apneic event, the person is unable to breathe in oxygen and to exhale carbon dioxide, resulting in low levels of oxygen and increased levels of carbon dioxide in the blood. The reduction in oxygen and increase in carbon dioxide alert the brain to attempt to resume breathing by causing what is termed an "arousal." With each arousal, a signal is sent from the brain to the upper respiratory airway muscles to open the airway; breathing is eventually resumed, often with a loud snort or gasp. Frequent arousals, although necessary for breathing to restart, prevent the patient from getting enough restorative deep sleep.

As a result of the serious disturbances in their normal sleep patterns, people with SA often feel extremely sleepy during the day and, as such, their concentration and daytime performance suffer. The consequences of SA range from annoying to life-threatening. They include symptoms of depression, irritability, sexual dysfunction and learning and memory difficulties, as well as falling asleep while at work, on the phone or driving. Untreated SA patients are at least three times as likely to encounter a dangerous condition or an accident as a result of SA, such as, for example, automobile or other machinery accidents. Moreover, it has been estimated that up to fifty percent of SA patients have high blood pressure. Finally, it has recently been shown that the risk for heart attack and stroke may also be increased in those with SA.

The specific therapy for SA is tailored to the individual patient based on medical history, physical examination and the results of any polysomnographic tests done on the patient. Medications are generally not effective in the treatment of SA.

Nasal continuous positive airway pressure (CPAP) is the most common effective treatment for SA. In this procedure, the patient wears a mask (sometimes referred to as a CPAP sleeve or device) over the head during sleep, and pressure from an air blower forces air through the nasal passages. The air pressure is variably adjusted so that it is just enough to prevent the throat from collapsing during sleep. The pressure is continuous and constant.

Variations of CPAP devices attempt to minimize side effects that sometimes occur, such as nasal irritation and drying, facial skin irritation, abdominal bloating, mask leaks, sore eyes and headaches. Some versions of CPAP devices vary the pressure to coincide with the person's breathing pattern, and other CPAP devices start with low pressure, slowly increasing it to allow the person to fall asleep before the full prescribed pressure is applied.

An example of such a mask is illustrated in FIG. 1. As shown in FIG. 1, mask 10 comprises top strap 12 and bottom strap 14. Top strap 12 and bottom strap 14 securely and snugly hold nosepiece 16 to the face of wearer 18. Pressurized air is forced from an air blower (not shown) through breathing tube 20 into the nasal respiratory airway of wearer 18 in an attempt to keep the nasal respiratory airway open. While the prior art disclosed in FIG. 1 attains the goal of forcing air through the nasal respiratory airway, it does not inhibit the use of the mouth for breathing.

To inhibit such a use of the mouth, sleep apnetics have come to wear chinstraps, such as that illustrated by FIG. 2. In FIG. 2, chinstrap 22 is illustrated as comprising chin portion 24 and adjustable strap portion 26. Wearer 18, when using chinstrap 22, adjusts adjustable strap portion 26 to provide a snug fit of chin portion 22 on the chin of wearer 18. This maintains a closed mouth during sleep, forcing wearer 18 to breathe only through the nose. Additionally, chin portion 22 defines chin portion opening 28. Another example of such a chinstrap device is disclosed in U.S. Pat. No. 5,361,416, issued to Petrie et al. However, like the mask illustrated in FIG. 1, the chinstrap illustrated in FIG. 2 and in Petrie only address one aspect of SA; that being the inhibition of the use of the mouth during sleep. See, e.g., Petrie, Abstract.

Thus, although such devices attempting to cure SA do exist, the devices in existence suffer from a number of disadvantages. Most noticeable is the fact that neither device can completely assist the wearer in treating SA or any other oxygen-deprivation disorders. For instance, wearing the mask illustrated in FIG. 1 does not force the mouth of the wearer closed during sleep. Likewise, wearing the chinstrap illustrated in FIG. 2 does not ensure the nasal respiratory airways will remain open during sleep. Instead, some sleep apnetics have had to resort to wearing combinations of both the mask and the chinstrap.

However, even the simultaneous use of the mask and the chinstrap, as presently known, has its disadvantages. First and foremost, effectiveness is a major issue. Experiments have shown that one or both of the devices tends to slip off the wearer's head during sleep, causing the same ineffective situation as if the wearer had been wearing only one of the devices. Secondly, the presence of extra straps on the face leads to an improper fit of the nosepiece to the wearer's nose. Comfort is an additional factor—the use of both devices simultaneously has caused, in experiments, chafing and other friction-based indications on the wearer's face.

Thus, the need exists for an improved headgear apparatus for effectively treating the symptoms of SA (and other oxygen deprivation disorders), while at the same time overcoming the above-stated disadvantages.

SUMMARY OF THE INVENTION

The headgear apparatus of the present invention is designed to secure, to the face of the wearer, most present types of "on the face" respiratory paraphernalia. More specifically, the headgear apparatus of the present invention is designed to secure the three primary types of "on the face" respiratory paraphernalia and devices that are used in CPAP therapy that require chinstraps, including, for example, CPAP nose masks, CPAP nasal pillows and Cannula nasal pillows. Advantageously, the headgear apparatus of the present invention provides a more functional, stable, convenient and comfortable method of securement than the methods currently being used and described above. To meet these advantages, the headgear apparatus of the present invention incorporates the mask and chinstrap, described above, into a single (and one piece) design that is additionally light-weight, strong and comfortable.

Moreover, the devices that the headgear apparati, described herein, secure to the face of the wearer deliver strong blasts of air through the nosepiece portions to the respiratory airways of people who suffer with sleep disorders including, without limitation, SA. These blasts of air keep respiratory airways open during sleep. The current combination method of securing the nosepiece portions is a separate mask to secure the breathing device to the face and a separate chinstrap to hold the mouth closed during sleep. The present invention, therefore, provides an advantage over the above-described current methods.

To this end, the present invention comprises a headgear apparatus comprising a sleeve, a first strap portion and a second strap portion. The sleeve comprises a chin portion and a top portion. The top portion is integrally connected to the chin portion. The first strap portion is connected to a first part of the sleeve near the top portion. The second strap portion is connected to a second part of the sleeve near the chin portion. A nosepiece may be fastened to the headgear apparatus via the first strap portion and the second strap portion.

As will be shown, the present invention comprises a headgear apparatus with at least ten important features. First, the present invention incorporates the mask and the chinstrap, described above, into a single, one-piece unit. The single unit design makes the headgear apparatus more convenient to use and more stable. It is also more comfortable to wear than the disclosed combination.

Second, the present invention provides three chinstrap options, two "floating" and one detachable. Utilizing these options, in addition to performing its regular function of securing the headgear apparatus to the face, the chinstrap moves independently of the sleeve to hold the mouth closed during sleep. All three options can be adjusted separately without affecting the other aspects of the headgear apparatus, thus alleviating any worry about the sleeve causing discomfort in the jaw area or at various pressure points around the face of the wearer.

Third, the present invention comprises a "one size fits all" headgear apparatus, primarily through the use of friction closures (e.g., Velcro) located at the top, the back and the neck of the headgear apparatus. Additionally, the "floating" chinstraps, disclosed above, can also be adjustable, at both the chin as well as the top of the head. Finally, the angle and length of each of the individual strap portions make it possible to adjust the mask portion to fit any size face.

Fourth, the present invention provides additional strength and stability than the current methods for securing the sleeve to the face. In the present invention, the base of the sleeve is located closer to the face. Since the straps that secure the nosepiece portion are attached to the base, they hold more securely by virtue of being shorter.

Fifth, the front straps of the present invention can be secured at various angles on the sleeve. This helps to slightly reposition the nosepiece portion on the face to help prevent air leaks.

Sixth, the present invention offers an optional, unattached strap. This optional strap can be used to add pressure to the center of the nosepiece portion. The center of this strap is secured to the center of the nosepiece portion with an adhesive strip. The ends of the strap are then brought to either side of the sleeve and secured with a frictional closure. The added pressure on the nosepiece portion keeps it stable and helps prevent leaks.

Seventh, wearing the present invention is relatively easy. The sleeves have back and/or bottom openings so the nosepiece portion can be secured in position and remain on the sleeve. The existing headgear has a front entrance. The mask must be repositioned each time the wearer enters or exits the headgear.

Eighth, the present inventions holds any "on the face" breathing device more securely. When the breathing devices are stable, there are less air leaks, even when changing positions during sleep. The sleeve is especially beneficial to people with more complex or acute sleep disorders who require a stronger airflow to keep respiratory airways open during sleep. The stronger airflow can cause standard headgear to shift, causing air leaks and interrupted sleep. The wearer will experience irritation under the nose and air leaking into the eyes causing sore, red eyes and/or the need to adjust the headgear and/or nosepiece portion. The present invention, due to a more solid design, eliminates air leaks and shifting.

Ninth, the present invention provides for an embodiment to hold the tubing for the nasal oxygen cannulas in a more secure and comfortable way. Currently, the tubing is wrapped around the ears. The present invention keeps the tubing off tender skin in a practical manner, and can be customized and/or personalized.

Tenth, the present invention can be worn for any length of time without discomfort. There are no uncomfortable pressure points on the face, head, neck or ears. As a result, the present invention promotes better patient compliance.

These and other advantages of the present invention will be further understood and appreciated upon consideration of the following detailed description of embodiments of the invention taken in conjunction with the drawings, in which:

DETAILED DESCRIPTION OF THE PRESENTLY-PREFERRED EMBODIMENTS

Figure 1:
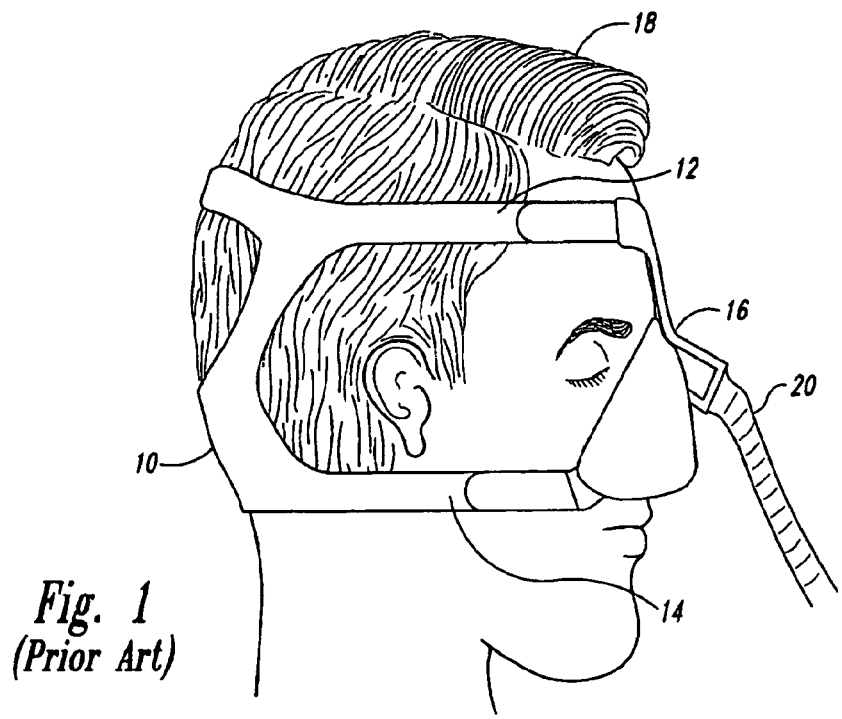
FIG. 1 illustrates an existing embodiment of a mask used for treating sleep apnea and other oxygen deprivation disorders.
Figure 2:
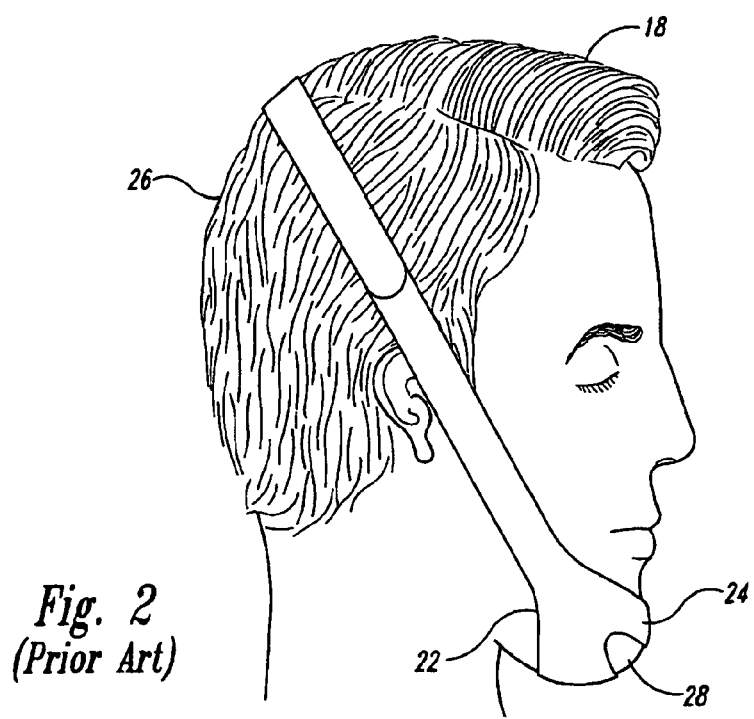
FIG. 2 illustrates an existing embodiment of a chinstrap used for treating sleep apnea and other oxygen deprivation disorders.
Figure 3:
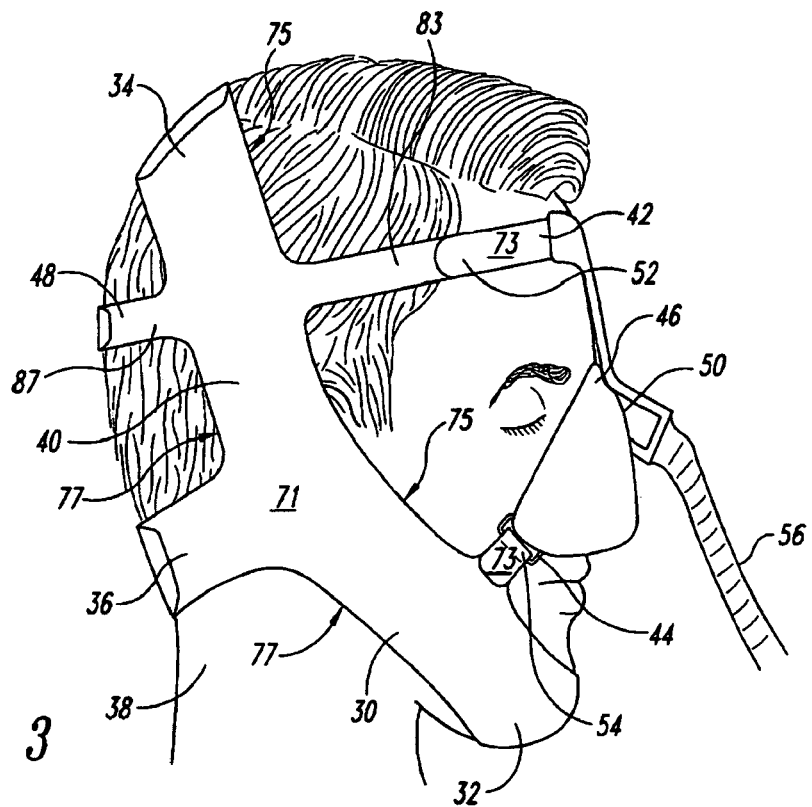
FIG. 3 illustrates one embodiment of a headgear apparatus used for treating sleep apnea and other oxygen deprivation disorders, made in accordance with the present invention.

FIGS. 3-6 illustrate embodiments of a headgear apparatus comprising, inter alia, a chin portion, a top portion and a neck portion. It should be noted that, although a substantial part of the discussion, both above and below, centers around the disorder of SA, the present invention is contemplated as additionally assisting in the treatment of various other oxygen-deprivation disorders. The present invention incorporates the mask and chinstrap, described above, into a single, one piece design that is strong, light-weight and extremely comfortable As shown in FIG. 3, which illustrates one embodiment of the present invention, headgear apparatus 30 comprises chin portion 32, first end 34 and strap portion 36. Preferably, the chin portion 32, as shown, conforms to the chin of wearer 38, and provides a snug fit of headgear apparatus 30 with wearer 38. Likewise, first end 34 conforms to the top of the head of wearer 38, and first strap portion 36 conforms to the back of the head of wearer 38, preferably near the neck. Collectively, chin portion 32, first end 34 and strap portion 36 may be referred to as sleeve 40.

Sleeve 40 provides a solid base for chin portion 32, first end 34 and strap portion 36. Preferably, sleeve 40 having an outer or first planar surface 71 and an inner or second planar surface 73 is wide enough to comfortably cover the ears, neck and chin of wearer 38 between a front edge 75 and a rear edge 77 of the sleeve 40, in addition to assisting in the stabilization of headgear apparatus 30 to the head of wearer 38. Additionally, the width of the various aspects of sleeve 40 between a front edge 75 and a rear edge 77 of the sleeve 40 is such that it ensures that there is neither any irritation of the face, nor does it contribute to the uncomfortableness, of wearer 38. Moreover, sleeve 40 is designed so that any pressure on the head, neck or ears of wearer 38 are abated.

Chin portion 32 engages the lower part of the chin of wearer 38 and provides a secure fit with wearer 38, while also preventing the opening of the mouth of wearer 38. Use of chin portion 32 ensures that wearer 38 breathes only through the nose during sleep. Although shown as a solid portion, chin portion 32 may be configured to possess an opening, or relief, into which wearer 38 may place the extreme portion of the chin. Additionally, a first strap portion 36 extends from the rear edge 77 to engage a second strap portion (obscured by the wearer 38) also extending from the rear edge 77 cooperating to enclose the rear of the head of the wearer 38). A more detailed discussion of such a chin relief portion is described with reference to FIG. 5, below.

Although not illustrated in the Figures, various variations of chin portion 32 are contemplated. First, chin portion may be integrated into a "floating" chinstrap. The "floating" chinstrap variation comprises a modified, tubular-styled sleeve (not shown). This sleeve (not shown), as modified, encases chin portion between two layers of the sleeve and allows the "floating" chinstrap to be moved, or floated, within the sleeve. As the modified sleeve can be adjusted without affecting the fit of the "floating" chinstrap, this movement of the "floating" chinstrap is independent of any movement of the sleeve. An alternative to this variation of the "floating" chinstrap comprises a chinstrap that is woven through the sleeve 40, similar as a belt is woven through belt loops. Another possible variation concerns a detachable chin portion (not shown). Chin portions made of a friction-dependent adhesive material also known as hook and loop fasteners, such as Velcro, may be detachable to the rest of the sleeve 40. This detachable chin portion (not shown) allows the removable chin portion to be placed at any angle or height on the sleeve, as well as to be adjusted independent of the sleeve. Moreover, because both the sleeve and the detachable chin portion (not shown) may be adjusted for fit and comfort separately and independently, less emphasis is on the positioning of the first and second strap portions vis a vis the face of wearer 38.

The first end 34 is used to secure headgear apparatus 30 to the top of the head of wearer 38. The first end 34 may also possess a top portion closing mechanism (not shown) for engaging a second end (not shown), which is used for adjusting headgear apparatus 30 to the head of wearer 38. That is, headgear apparatus 30 may be adjusted smaller or larger by selectively engaging the first end 34 with the second end (not shown) by means of the top closing mechanism (not shown) to comfortably accommodate the head of wearer 38. In this way, top portion closing mechanism (not shown) allows the headgear apparatus to be "one-size-fits-all." Additionally, by adjusting headgear apparatus 30 at the top of the head of wearer 38, sleeve 40 is stabilized, which gives support to third strap portion 42 and fifth strap portion 44 (described below) which cooperate with a fourth and a sixth strap portion (neither shown being obscured by the head of the wearer 38) to stabilize the breathing apparatus. When third strap portion 42 and fifth strap portion 44 are stable, they hold breathing apparatus 46 securely on the face of wearer 38, preventing both air leaks from a breathing apparatus 46, including a cup 50 and a hose 56 and from shifting on the face of wearer 38.

The first strap portion 36 is used to secure headgear apparatus 30 at the neck of wearer 38. The first strap portion 36 may also possess a neck portion closing mechanism (not shown), which is similar in both use and appearance as top portion closing mechanism. Similarly, by adjusting the first strap portion 36 engaging a second strap portion (not shown) by means of the closing mechanism (not shown) securing the headgear apparatus 30 against the back of the head of wearer 38, stabilization breathing apparatus 46 by means of both the third strap portion 42 in cooperation with the fourth strap portion and fifth strap portion 44 in cooperation with the sixth strap portion is achieved. This further assists in holding breathing apparatus 46 securely on the face of wearer 38, preventing both air leaks from breathing apparatus 46 and any shifting of breathing apparatus 46 on the face of wearer 38. Further stabilization of headgear apparatus 30 may be achieved through the use of eighth strap portion 48 (further described below).

As used in the present invention, headgear apparatus also includes third strap portion 42 in cooperation with the fourth strap portion (not shown) and fifth strap portion 44 in cooperation with the sixth strap portion (not shown), in combination, preferably assist in securing cup 50 of breathing apparatus 46 to the nose of wearer 38. Both the third strap portion 42 and fifth strap portion 44 may be further adjustable by wearer 38, through first hook fastening flap 52 configured to double back on the first strap portion 83 exposing a portion of the second planar surface 73 as hook fasteners (not shown) engage the loop portion 87 of first planar surface 71 and second hook fastening flap 54 to similarly engage the loop portion 87 of the first planar surface 71, so as to provide the preferred snug fit of cup 50 to wearer 38. Both the third strap portion 42 and the fifth strap portion 44 are shown as being integral with sleeve 40. Alternatively, although not shown in the embodiment of FIG. 3, both first strap portion 42 and second strap portion 44 may be removably affixed to sleeve 40. In such a case, affixation may occur through the use of friction-dependent adhesives, such as, for example, Velcro™ hook and loop fasteners.

Alternatively, and shown in FIG. 3, the eighth strap portion 48 in engagement with the ninth strap portion (not shown obscured by the wearer) may be used to further stabilize headgear apparatus 30. Moreover, the eighth strap portion 48, because it is located directly opposite to third strap portion 42 and fifth strap portion 44, may also assist in the stabilization of the breathing apparatus secured in cooperation between third strap portion 42 and the fourth strap portion (not shown) and the fifth strap portion 44 in cooperation with the sixth strap portion (not shown). When such stabilization occurs, breathing apparatus 46 is held to the face of wearer 38 more securely, again (similar to the aforementioned adjusting, closing or stabilizing devices) preventing shifting of breathing apparatus, as well as potential air leaks from breathing apparatus 46. Additionally, the eighth strap portion 48 may also include an eight and ninth strap portion closing mechanism (not shown) adjustably engaging the eight and ninth strap portions which, like the aforementioned closing mechanisms, allows for adjustments to be made for the purpose of the fit and comfort of wearer 38.

Finally, as shown in FIG. 3, the hose 56 may be attached to the cup 50 of breathing apparatus 46 to provide air to wearer 38. Generally speaking, the breathing apparatus 46, and all components thereof, are contemplated as being any breathing apparati currently existing and in use in the art. Thus, headgear apparatus 30, as described herein, may be used in conjunction with various types of breathing apparati.

Preferably, headgear apparatus 30 (which includes sleeve 40 and first, third, fifth, and eighth strap portions 36, 42, 44, 48 along with the respective strap portions with which they engage) primarily is comprised of any soft fabric-like material which may be comfortably worn by wearer 38 without undue stress, strain, pain or friction to wearer 38. Preferably, the second planar surface 73 the material of sleeve 40 in contact with the skin of wearer 38 is smooth, so as to not irritate or chafe the skin of wearer 38. The first planar surface 71 of the material of sleeve 40 may comprise a type of fabric-like adhesive, such as, for example, the female side or loop portion 87 of Velcro™ material. This is so that various aspects of headgear apparatus 30, such as first, third, fifth, and eighth strap portions 36, 42, 44, 48, for example, which preferably comprise an opposing type of fabric-like adhesive—such as the male side or hook portion of Velcro™ material, may be suitably affixed to the outer side of the material. In any event, the material ultimately used for headgear apparatus 30 should breathe and be able to be worn comfortably for an unlimited duration by wearer 38, without undue stress, strain or friction to wearer 38. Alternative to the Velcro™ hook and loop fastener "system," described above, other methods for securing portions of headgear apparatus 30 together include, for example, buttons, snaps, clips, etc.

Figure 4:
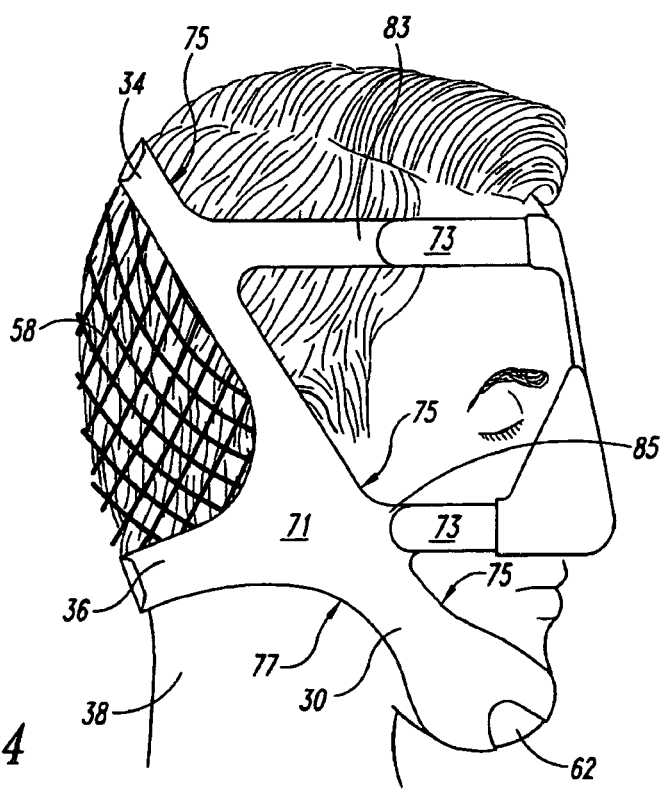
FIG. 4 illustrates another embodiment of a headgear apparatus used for treating sleep apnea and other oxygen deprivation disorders, made in accordance with the present invention.

FIG. 4 shows a second embodiment of headgear apparatus 30. More specifically, FIG. 4 shows a variation of the headgear apparatus. In the embodiment shown in FIG. 4, mesh portion 58 is shown as disposed between first end 34 and first strap portion 36 and further shows the omission of the optional eighth strap portion 48 for which the mesh portion 58 is a substitution. The mesh portion 58 is another option of the present invention, and further provides comfort of headgear apparatus 30 to wearer 38, as well as assists further in the stabilization of headgear apparatus 30.

Figure 5:
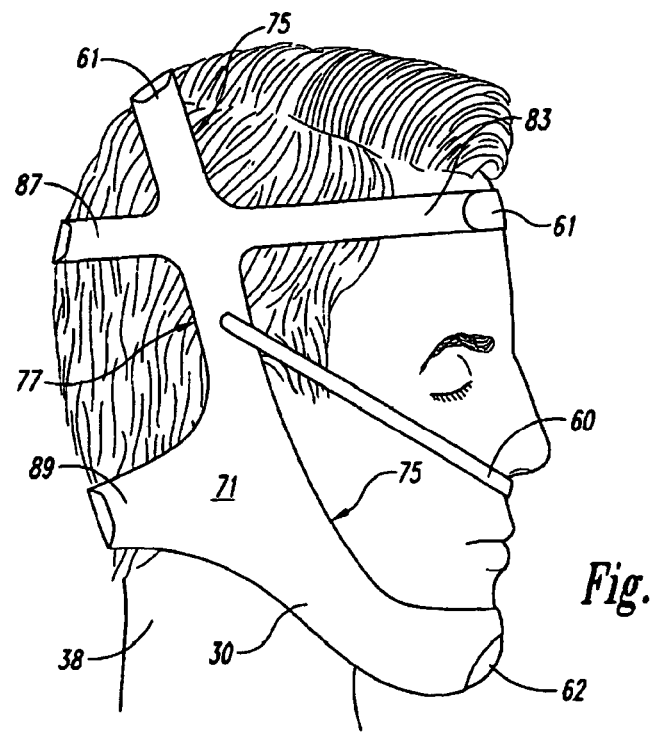
FIG. 5 illustrates yet another embodiment of a headgear apparatus used for treating sleep apnea and other oxygen deprivation disorders, made in accordance with the present invention.

FIG. 5 illustrates yet another embodiment of headgear apparatus 30. FIG. 5 differs from FIGS. 3-4 in that the embodiment shown in FIG. 5 comprises a tenth strap portion 60 engaging the sleeve 40 at the first planar surface 71 and extending past the front edge 75. In practice, the embodiment disclosed in FIG. 5 is preferably used in conjunction with a CPAP nasal pillow device, the tenth strap portion 60, as shown, fits below the nose of wearer 38. Moreover, the tenth strap portion 60 connects directly to headgear apparatus 30, as shown in FIG. 5; and can be detachable from headgear apparatus 30. Connection of the tenth strap portion 60 with headgear apparatus 30 may be by any known type of connector (not shown). Although not shown, connector may be any type of connecting device sufficient to secure fourth strap portion 60 to headgear apparatus 30, though as described in conjunction with FIGS. 3 and 4 the presently preferred embodiment includes the use of hook and loop fasteners on the first and second planar faces 71 and 73 respectively. In operation, the tenth strap portion 60 serves to secure and stabilize nosepiece portion (not shown in FIG. 5) to the face of wearer 38.

Additionally, shown in the embodiment of FIG. 5, although possible on all of the embodiments of the present invention, is chin relief portion 62 (as described above). The chin relief portion 60 is an aperture for transferring pressure away from an extreme edge of the chin for greater comfort.

Additionally, the embodiment shown in FIG. 5 indicates an alternative way for headgear apparatus 30 to secure the hose (not shown). Closures 61 secure the hose (not shown) to the first strap portion 83 extending from the front edge 75 by means of loop surfaces 87, 89 of the headgear apparatus 30. An alternative first end 61 is moved slightly forward relative to the first end 34 (FIGS. 3. 4) on the head to provide maximum comfort to the wearer.

Figure 6:
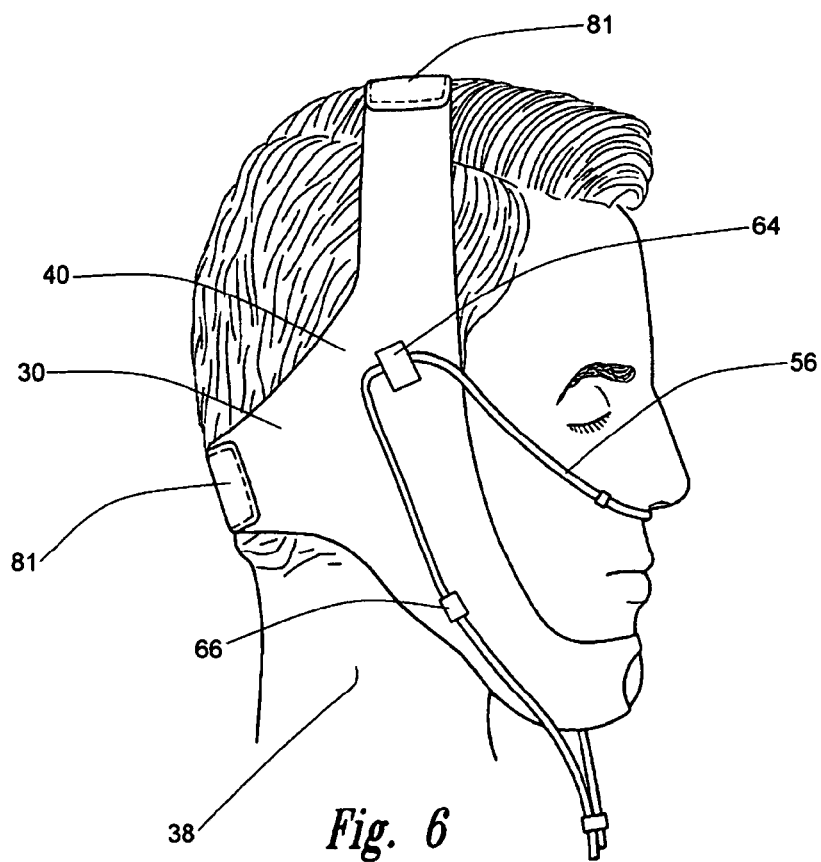
FIG. 6 illustrates yet another embodiment of a headgear apparatus used for treating sleep apnea and other oxygen deprivation disorders, made in accordance with the present invention.

Finally, FIG. 6 illustrates yet another embodiment of headgear apparatus 30. The embodiment shown in FIG. 6 illustrates headgear apparatus 30 as used with the Cannula style of nasal pillow devices. Breathing tube 56 is attached to sleeve 40 of headgear apparatus 30 by the combination of first channel 64 and second channel 66. Both first channel 64, near the ear of wearer 38, and second channel 66, near the neck of wearer 38, are open at both ends. The first channel is formed by flaps 81 turned back over the breathing tube 56 such that hook fabric swatches affixed to the first planar surface 71 engage the loop surface 89 exposing the second planar surface 73. The second channel is likewise formed by flaps 81 turned back over the breathing tube 56 such that hook fabric swatches affixed to the first planar surface 71 engage the loop surface 89 exposing the second planar surface 73. In operation, breathing tube 56 is fed through each of first channel 64 and second channel 66. Breathing tube 56 is then met with a breathing tube (not shown) from the opposing side of the face of wearer 66 and continues down in an area of a chest of wearer 38. Note that the breathing tube on the opposing side of the face is also fed through similar channels. Alternatively, second channel 38 may be configured such that breathing tube 56 connects with the opposing breathing tube on the back of wearer 38.

FIG. 5 illustrates yet another embodiment of headgear apparatus 30. FIG. 5 differs from FIGS. 3-4 in that the embodiment shown in FIG. 5 comprises a tenth strap portion 60 engaging the sleeve 40 at the first planar surface 71 and extending past the front edge 75. In practice, the embodiment disclosed in FIG. 5 is preferably used in conjunction with a CPAP nasal pillow device, The tenth strap portion 60, as shown, fits below the nose of wearer 38. Moreover, the tenth strap portion 60 connects directly to headgear apparatus 30, as shown in FIG. 5, and can be detachable from headgear apparatus 30. Connection of the tenth strap portion 60 with headgear apparatus 30 may be by any known type of connector (not shown). Although not shown, connector may be any type of connecting device sufficient to secure tenth strap portion 60 to headgear apparatus 30, though as described in conjunction with FIGS. 3 and 4 the presently preferred embodiment includes the use of hook and loop fasteners on the first and second planar faces 71 and 73 respectively. In operation, the tenth strap portion 60 serves to secure and stabilize nosepiece portion (not shown in FIG. 5) to the face of wearer 38.

Additionally, shown in the embodiment of FIG. 5, although possible on all of the embodiments of the present invention, is chin relief portion 62 (as described above).

Additionally, the embodiment shown in FIG. 5 indicates an alternative way for headgear apparatus 30 to secure the hose (not shown). Closures 61 secure the hose (not shown) to the first strap portion 83 extending from the front edge 75 by means of loop surfaces 87,89 of the headgear apparatus 30. An alternative first end 61 is moved slightly forward relative to the first end 34 (FIGS. 3, 4) on the head to provide maximum comfort to the wearer.

Finally, FIG. 6 illustrates yet another embodiment of headgear apparatus 30. The embodiment shown in FIG. 6 illustrates headgear apparatus 30 as used with the Cannula style of nasal pillow devices. Breathing tube 56 is attached to sleeve 40 of headgear apparatus 30 by the combination of first channel 64 and second channel 66. In operation, breathing tube 56 is fed through each of first channel 64 and second channel 66. Breathing tube 56 is then met with a breathing tube (not shown) from the opposing side of the face of wearer 38 and continues down in an area of a chest of wearer 38. Note that the breathing tube on the opposing side of the face is also fed through similar channels (not shown). Alternatively, second channel 66 may be configured such that breathing tube 56 connects with the opposing breathing tube on the back of wearer 38.

The friction closers 81 at the top of the head and at the back of the neck make it easy to adjust the sleeve to give the headgear apparatus 30 a custom fit. As a result, the sleeve holds to wearer 38 very securely. Headgear apparatus 30, of the present invention, has a wider band, especially covering the ear. This makes headgear apparatus 30 very comfortable and allows it to be worn for an unlimited period of time. There are no uncomfortable pressure points and, thus, headgear apparatus 30 is very comfortable to wear to bed. Headgear apparatus 30 holds the cannula in place comfortably and securely and won't shift when changing positions during sleep. Moreover, the headgear apparatus 30 can be formed in various styles to which the tubing may be secured. The material utilized in the construction of the headgear apparatus 30 may be made of mesh panels that are lightweight and cool. The tubing is secured to the headgear apparatus 30 by routing the tubing through channels 64 and 66 which may be formed using small friction-based adhesives on either side of the cap. The tubing may be secured to the headgear apparatus 30 with either decorative or plain adhesives, or, alternatively, through the use of clips.

Now, referring to FIGS. 3-6, the present invention may be installed on the wearer 38 utilizing at least three entrance options including a rear entrance, a bottom entrance, and a back entrance. In the rear entrance option, the sleeve 40 possesses a strap 48 at the center back of the head of wearer 38 that secures and stabilizes the headgear apparatus 30. Friction-based adhesives on the center back of the neck make it easy to enter and/or exit the headgear apparatus 30 without removing the mask from the sleeve. In the bottom entrance option, the sleeve 40 includes a stretch mesh panels positioned at the back of the head of the wearer 38. The panel 58 secures the sleeve 40 and helps anchor the strap portions. Friction-based adhesive at the back of the neck make it possible to enter and exit from the bottom, in ski mask fashion. Once in place, the breathing apparatus 46 stays on the sleeve when entering and exiting the sleeve. In the back entrance option, the center back, neck straps, and one apparatus friction-based adhesive has been eliminated. After the initial adjustment for fit is made, the breathing apparatus 46 can remain on the headgear apparatus 30. The friction-based adhesive can be opened when entering or exiting the sleeve 40 from the back, or the adhesive can remain closed to enter or exit from the bottom. Advantageously, no further adjustments are necessary to the friction-based adhesive until it is time for a new sleeve. Moreover, if the sleeve 40 possesses a detachable chinstrap, and after initial adjustments have been made for fit and position of the nosepiece portion 50, the wearer 38 may remove the chinstrap to enter and/or exit the sleeve 40 from the bottom or leave the chinstrap in place to enter and/or exit the sleeve 40 from the back. In either option here, the nosepiece portion 50 will remain in place on the sleeve when entering and/or exiting.

Although preferred embodiments of the invention have been described in the foregoing description and illustrated in the accompanying drawings, the invention is not intended to be limited to the specific embodiments disclosed, but is capable of numerous changes, rearrangements and modifications without departing from the scope of the invention. Accordingly, the claims hereafter to the present invention are intended to encompass such changes, rearrangements and modifications as fall within the scope of the invention.

What is claimed is:

1. A headgear apparatus for receiving a human head, the headgear comprising:
   a sleeve having a substantially planar first surface, a substantially planar second surface parallel to and spaced apart from the substantially planar first surface, a front edge, a rear edge comprising:
   a substantially elongate strap portion including:
      a chin portion configured to engage a human chin;
      a first end including a first friction fastener female surface on the first surface; and
      a second end including a first friction fastener male surface on the second surface configured to engage the first friction fastener female surface while resting substantially on a crown of the human head;
   a first strap portion continuing from the sleeve substantially midway between the chin portion and the first end extending from the rear edge and terminating at a first extremity; and
   a second strap portion continuing substantially midway between the chin portion and the second end, and extending from the rear edge and terminating at a second extremity, the second extremity configured to fasten to the first extremity to engage at a rear of the human head.

2. The headgear apparatus of claim 1, wherein:
   the friction fastener female surface includes a loop surface configured to engaged a hook surface in removably fastened relationship; and
   the friction fastener male surface includes the hook surface configured to engage the loop surface in removably fastened relationship.

3. The headgear apparatus of claim 1, wherein the sleeve further comprises:
   a third strap portion continuing from the sleeve substantially midway between the
   chin portion and the first end extending from the front edge and configured to engage a respiratory device assembly; and
   a fourth strap portion continuing from the sleeve substantially midway between the chin portion and the second end extending from the front edge and configured to engage the respiratory device assembly and in concert with the third strap to hold the respiratory device assembly in a position in operative proximity to a nose on the human head.

4. The headgear apparatus of claim 3, further comprising:
   a fifth strap portion continuing from the sleeve at the front edge, spaced apart from and substantially parallel to the third strap configured to engage the respiratory device assembly; and
   a sixth strap portion continuing from the sleeve at the front edge, spaced apart from and substantially parallel to the fourth strap and configured to engage the respiratory device assembly and in concert with the third, fourth, and fifth strap portions to hold the respiratory device assembly in operative proximity to the nose.

5. The headgear apparatus of claim 3, further comprising a seventh strap portion continuing from the first end from the front edge and configured to engage the respiratory device assembly and in concert with the third and fourth strap portions to hold the respiratory device assembly in operative proximity to the nose.

6. The headgear apparatus of claim 3, further comprising a seventh strap portion continuing from the second end from the front edge and configured to engage the respiratory device assembly and in concert with the third and fourth strap portions to hold the respiratory device assembly in operative proximity to the nose.

7. The headgear apparatus of claim 1, wherein the chin portion defines a chin relief aperture.

8. The headgear apparatus of claim 1, wherein the first surface is first friction fastener female surface.

9. The headgear apparatus of claim 1, wherein the respiratory device is a positive airway pressure mask.

10. The headgear apparatus of claim 1, wherein the respiratory device is a positive airway pressure nasal pillow.

11. The headgear apparatus of claim 1, wherein the respiratory device is a nasal cannula.

12. The headgear apparatus of claim 1, wherein:
    a eighth strap portion substantially parallel to and spaced apart from the first strap portion continuing from the sleeve, from the rear edge between the first strap portion and the chin portion extending from the rear edge and terminating at a eighth extremity; and
    a ninth strap portion substantially parallel to and spaced apart from the first strap portion continuing from the sleeve, from the rear edge midway between the second strap portion and the chin portion and terminating at a ninth extremity, the ninth extremity configured to fasten to the eighth extremity to engage at the rear of the human head.

13. A headgear apparatus for receiving a human head, the headgear comprising:
    a sleeve having a substantially planar first surface, a substantially planar second surface parallel to and spaced apart from the substantially planar first surface, a front edge, a rear edge comprising:
    a substantially elongate strap portion including:
       a medial portion configured to engage a crown of the human head;
       a first end including a first friction fastener female surface on the first surface; and
       a second end including a first friction fastener male surface on the second surface configured to engage the first friction fastener female surface while resting substantially on a chin of the human head;
    a first strap continuing from the sleeve substantially midway between the medial portion and the first end extending from the rear edge and terminating at a first extremity; and
    a second strap portion continuing substantially midway between the medial portion and the second end, and extending from the rear edge and terminating at a second extremity, the second extremity configured to fasten to the first extremity to engage at a rear of the human head.

14. The headgear apparatus of claim 13, wherein:
    the friction fastener female surface includes a loop surface configured to engaged a hook surface in removably fastened relationship; and the friction fastener male surface includes the hook surface configured to engage the loop surface in removably fastened relationship.

15. The headgear apparatus of claim 13, wherein sleeve further comprises:
   a third strap portion continuing from the sleeve substantially midway between the
   medial portion and the first end extending from the front edge and configured to engage a respiratory device assembly; and
   a fourth strap portion continuing from the sleeve substantially midway between the medial portion and the second end extending from the front edge and configured to engage the respiratory device assembly and in concert with the third strap to hold the respiratory device assembly in a position in operative proximity to a nose on the human head.

16. The headgear apparatus of claim 15, further comprising:
   a fifth strap portion continuing from the sleeve at the front edge, spaced apart from and substantially parallel to the third strap configured to engage the respiratory device assembly; and
   a sixth strap portion continuing from the sleeve at the front edge, spaced apart from and substantially parallel to the fourth strap and configured to engage the respiratory device assembly and in concert with the third, fourth, and fifth strap portions to hold the respiratory device assembly in operative proximity to the nose.

17. The headgear apparatus of claim 16, further comprising a seventh strap portion continuing from the medial portion, from the front edge and configured to engage the respiratory device assembly and in concert with the third and fourth strap portions to hold the respiratory device assembly in operative proximity to the nose.

18. The headgear apparatus of claim 13, wherein the first surface is first friction fastener female surface.

19. The headgear apparatus of claim 13, wherein the respiratory device is a positive airway pressure mask.

20. The headgear apparatus of claim 13, wherein the respiratory device is a positive airway pressure nasal pillow.

21. The headgear apparatus of claim 13, wherein the respiratory device is a nasal cannula.

22. The headgear apparatus of claim 13, wherein:
   an eighth strap portion substantially parallel to and spaced apart from the first strap portion continuing from the sleeve, from the rear edge between the first strap portion and the medial portion extending from the rear edge and terminating at a eighth extremity; and
   a ninth strap portion substantially parallel to and spaced apart from the first strap portion continuing from the sleeve, from the rear edge midway between the second strap portion and the medial portion and terminating at a ninth extremity, the ninth extremity configured to fasten to the eighth extremity to engage at the rear of the human head.

23. The headgear apparatus of claim 13, wherein:
   a mesh fabric extends from the rear edge configured to substantially cover a crown aperture, the crown aperture defined by the rear edge extending from the first extremity through the medial portion and to the second extremity when the second extremity is fastened to the first extremity.

* * * * *